United States Patent [19]

Kawashima et al.

[11] Patent Number: 4,556,738

[45] Date of Patent: Dec. 3, 1985

[54] PROCESS FOR PREPARATION OF 3,3'- OR 3,4'-DIAMINO BENZOPHENONE

[75] Inventors: Saburo Kawashima, Yokosuka; Akihiro Yamaguchi, Kamakura, both of Japan

[73] Assignee: Mitsui Toatsu Chemicals, Inc., Tokyo, Japan

[21] Appl. No.: 454,973

[22] Filed: Jan. 3, 1983

[30] Foreign Application Priority Data

Jan. 12, 1982 [JP] Japan ................................. 57-2255
Jan. 25, 1982 [JP] Japan ................................. 57-8829
Mar. 24, 1982 [JP] Japan ................................. 57-45691
Apr. 13, 1982 [JP] Japan ................................. 57-60273
May 21, 1982 [JP] Japan ................................. 57-84890
Jul. 17, 1982 [JP] Japan ................................. 57-123775

[51] Int. Cl.$^4$ ............................................ C07C 97/10
[52] U.S. Cl. .................................... 564/329; 564/411; 564/412
[58] Field of Search ................ 564/329, 411, 412, 328

[56] References Cited

U.S. PATENT DOCUMENTS 2,525,508 10/1950 Zimmerman ........................ 564/411
3,213,139 10/1965 Chase et al. ........................ 564/329
3,215,737 11/1965 Nelson et al. ...................... 564/329
3,711,552 1/1973 Foster et al. ....................... 564/411
3,988,300 10/1976 Cross ............................... 564/329 X

*Primary Examiner*—Robert V. Hines
*Attorney, Agent, or Firm*—Kane, Dalsimer, Kane, Sullivan and Kurucz

[57] ABSTRACT 3,3'- or 3,4'-diamino benzophenone is prepared by catalytically reducing and dehalogenating, in the presence of a reduction catalyst and a dehydrohalogenation agent, a benzophenone compound or benzophenone compounds of the general formula

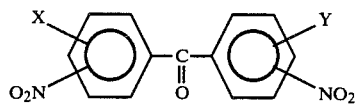

in which X is a halogen atom at position 2 or 4 of the benzene ring and Y is hydrogen or a halogen atom and in which the nitro group is at position 3' or 4' of the benzene ring if Y is hydrogen, while Y is at position 4' and the nitro group is at position 3' of the benzene ring if Y is a halogen atom.

7 Claims, No Drawings

PROCESS FOR PREPARATION OF 3,3'- OR 3,4'-DIAMINO BENZOPHENONE

BACKGROUND OF THE INVENTION

The present invention relates to a novel process for preparing 3,3'- or 3,4'-diamino benzophenone.

3,3'- or 3,4'-diamino benzophenone is useful as monomers for heat-resistant polymers, agricultural or medical chemicals, intermediates for dyestuffs and the like. Particularly, they are important as raw materials for heat-resistant polyamide or polyimide resins.

In a conventional known process, 3,3'-diamino benzophenone is prepared by the reduction of 3,3'-dinitro benzophenone which has been prepared by the nitration of benzophenone. However, in the nitration reaction of benzophenone to 3,3'-dinitro benzophenone, there are required repeated refining operations by means of recrystallization for separating 3,3'-dinitro benzophenone from the reaction product containing impurities such as the isomers of the dinitro benzophenone (E. Barnatt et al., J. Chem. Soc., 125, 767 (1924)). Thus, the process is disadvantageous in that it produces only an extremely low yield of 3,3'-dinitro benzophenone and requires complicated operations for recovering the voluminous solvents used in the refining steps and for treating residuals, making the process uneconomical. The process has a further drawback in that the reduction of 3,3'-dinitro benzophenone to 3,3'-diamino benzophenone must be carried out using an excess amount of stannous chloride dissolved in a large amount of concentrated hydrochloric acid (L. H. Klemm et al., Org. Chem. 23, 351 (1958)), requiring the use of the costly stannous compound and the treatment of the spent metal and the spent acid. The process is therefore unsuitable for producing 3,3'-diamino benzophenone on a commercial scale, from the standpoint of both economy and environmental protection.

It has been conventionally known to prepare 3,4'-diamino benzophenone by the reduction of 3,4'-dinitro benzophenone. For preparing 3,4'-dinitro benzophenone, there have been known such processes as the process where 3,4'-dinitro diphenyl methane, which has been produced by the reaction of 4-nitro benzylalcohol and nitrobenzene, is oxidized by chromic acid (P. J. Montagne et al., Ber., 49, 2293–2294 (1916)), the process where diphenyl acetate is nitrated by fuming nitric acid to produce 3,4'-dinitro diphenyl acetate which is then oxidized by chromic acid (I. M. Hunsberger et al., J. Am. Chem. Soc., 71, 2635–2639 (1949)), and the process where 4-nitro benzophenone is nitrated (Vernon. L. Bell et al., J. Of Polymer Chem., 14, 2277 (1976)). However, these processes involve complicated reactions. They are also disadvantageous in that they require the repetition of refining operations by means of recrystallation for removing large amounts of by-products such as isomers, and further treatments of spent acids and/or metals, making the processes uneconomical. Thus, the 3,4'-dinitro benzophenones obtained by such processes cannot provide the raw materials for commercially producing 3,4'-diamino benzophenone.

It has been known to prepare 3,3'-dinitro-4,4'-dichloro benzophenone, one of the benzophenone derivatives to be used as starting material in the present invention, by the nitration of 4,4'-dichloro benzophenone. For example, it is known to nitrate 4,4'-dichloro benzophenone by nitric acid or sodium nitrate and sulfuric acid (E. R. Kofanav et al., J. Org. Chem. USSR, 15, 98–100 (1979)). However, such process has several drawbacks. For example, there is used a large amount of the mixed acid which must be subjected to a certain treatment after the completion of the reaction. Further, it is not easy to isolate the desired compound in a high purity from the reaction product, since the compound tends to take granular forms so as to bear the raw material and the acids therein. It is not easy to refine such compound after the completion of the reaction. It may be proposed to obtain the desired compound in a high purity by isolating said compound by means of filtering immediately after the crystallization from the mixed acid. However, such procedure is troublesome and impractical for commercial production of the desired compound. The prior art process has a further disadvantage from the standpoint of operational easiness and economy in that, as the nitration reaction is exothermal, the reaction must be carried out by adding the raw material stepwise in small doses to the reactor and/or cooling the reactor efficiently.

It has been therefore highly desired to develop a process for commercially producing 3,3'-dinitro-4,4'-dichloro benzophenone by the nitration of 4,4'-dichloro benzophenone in which the reaction heat can be controlled in an easy manner, there is used minimal amount of the mixed acid, the treatments after the reaction can be easily made, and further there can be obtained crystalline 3,3'-dinitro-4,4'-dichloro benzophenone in a high yield and purity.

SUMMARY OF THE INVENTION

It is an object of the present invention to provide a process for preparing 3,3'- or 3,4'-diamino benzophenone, which process is advantageous from the commercial standpoint, can produce the desired product in a high yield, and offers an easy treatment of waste liquids after the reaction.

It is another object of the present invention to provide a novel process for preparing 3,3'-dinitro-4,4'-dichloro benzophenone, as starting material for the above mentioned process, in a high yield and purity.

It is a further object to provide a process for preparing 3,3'- or 3,4'-diamino benzophenone in which the reaction intermediates can be applied to the subsequent reaction steps, without need of separation of various isomers therefrom.

According to the present invention, there is provided a process for preparing 3,3'- or 3,4'-diamino benzophenone which comprises catalytically reducing and dehalogenating, in the presence of a reduction catalyst and a dehydrohalogenation agent, a benzophenone compound or benzophenone compounds of the general formula

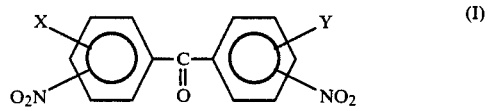 (I)

in which X is a halogen atom at position 2 or 4 of the benzene ring and Y is hydrogen or a halogen atom and in which the nitro group is at position 3' or 4' of the benzene ring if Y is hydrogen, while Y is at position 4' and the nitro group is at position 3' if Y is a halogen atom.

According to the present invention, there is also provided a process for preparing crystalline 3,3'-dinitro- 4,4'-dichloro benzophenone in a high yield and purity which comprises nitrating 4,4'-dichloro benzophenone in a fatty halogenated hydrocarbon solvent.

According to the present invention, there is further provided a process for preparing 3,3'-diamino benzophenone in a high yield which comprises reacting 2-chloro benzoylchloride and/or 4-chloro benzoylchloride with chlorobenzene by Friedle-Crafts' technique to produce a mixture of dichloro benzophenones, nitrating directly said mixture (i.e. without said mixture having been subject to any refining operation) to produce a mixture of dinitro dichloro benzophenones, and then catalytically reducing and dechlorinating said mixture of dinitrodichloro benzophenones in the presence of a reduction catalyst and dehydrochlorination agent to produce 3,3'-diamino benzophenone.

DETAILED DESCRIPTION OF THE INVENTION

The process of the present invention can produce 3,3'- or 3,4'-diamino benzophenone in a high yield at a lower cost, without causing the environmental pollution due to wastes. Furthermore, the desired compound can be isolated at a high purity from the reaction product, without need for complicated refining operations. Thus, the process of the present invention is very suitable for commercially producing 3,3'- or 3,4'-diamino benzophenone.

The nitration in the process of the present invention, where there is used a fatty halogenated hydrocarbon solvent, is advantageous in that the control of the reaction heat is carried out in an easy manner, the amount of the mixed acid used is smaller, and it is easy to recover the solvent for reuse if required. Thus, the process is effective for producing 3,3'-dinitro-4,4'-dichloro benzophenone in a high yield and purity.

According to the process of the present invention, it is also possible to produce 3,3'-diamino benzophenone from 2-chloro benzoylchloride and/or 4-chloro benzoylchloride as starting materials, where the products in the forms of mixtures containing various isomers produced in the intermediate steps can be directly applied to the subsequent steps without need of refining such products to separate the desired product therefrom.

It is known to prepare dichloro benzophenones through a Friedle-Crafts' reaction of chloro benzoic acid and chlorobenzene or chloro benzoyl chloride and chlorobenzene. For example, the reaction of 4-chloro benzoic acid and chlorobenzene in the presence of anhydrous aluminum chloride produces a mixture of 4,4'-dichloro benzophenone and 2,4'-dichloro benzophenone in a proportion of 82%:12% (H. P. Newton et al., Indust. And Eng. Chem., 27, 1397 (1935)). As another example, the reaction of 4-chloro benzoylchloride and chlorobenzene in the presence of anhydrous ferric chloride as catalyst produces a mixture of dichloro benzophenones with a yield of 90% where the proportion of 4,4'-dichloro benzophenone and 2,4'-dichloro benzophenone is 97–90%:3–10%. The mixture is refined by recrystallization to separate 4,4'-dichloro benzophenone, desired product, with a yield of 75% (E. R. Kofanov et al., J. Org. Chem. of USSR, 15, 98–100 (1979)). In a similar manner, the reaction of 2-chloro benzoyl chloride and chlorobenzene produces a mixture of 2,4'-dichloro benzophenone and 2,2'-dichloro benzophenone in a proportion of approx. 90%:10%.

Thus, the product of the Friedle-Crafts+ reaction of 2-chloro benzoylchloride and/or 4-chloro benzoylchloride with chlorobenzene is in the form of a mixture of various isomers. It is therefore necessary to isolate a desired dichloro benzophenone from such a mixture if it is intended to use the dichloro benzophenone as starting material for a specific product.

However, if nitration is conducted on a mixture of 4,4'-dichloro benzophenone, 2,4'-dichloro benzophenone and 2,2'-dichloro benzophenone (i.e. the product of the Friedle-Crafts' reaction of 2-chloro benzoylchloride and/or 4-chloro benzoylchloride with chlorobenzene), all the dichloro benzophenones are nitrated at their m- and m'-positions with respect to the carbonyl group to produce 3,3'-dinitro-4,4'-dichloro benzophenone, 5,3'-dinitro-2,4'-dichloro benzophenone and 5,5'-dinitro-2,2'-dichloro benzophenone, respectively, and all these dinitro-dichloro benzophenones will convert, through the reduction and dechlorination according to the present invention, to 3,3'-diamino benzophenone.

Thus, according to the process of the present invention in which there is produced 3,3'-diamino benzophenone through the three steps of the Friedle-Crafts' reaction, the nitration reaction and the reduction-dechlorination reaction from chlorobenzoylchlorides, the intermediates can be used in the production of 3,3'-diamino benzophenone without refining operations of such intermediates. The present invention therefore offers commercially acceptable low-cost process for the production of 3,3'-diamino benzophenone, because of easy operation and high yield and purity of the desired product.

The compound of the formula (I) as defined above can be expressed specifically in the following manners:

A benzophenone compound of the general formula

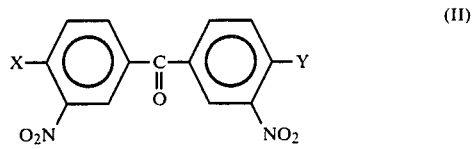

in which X and Y are the same or different halogen atoms;

A benzophenone compound of the general formula

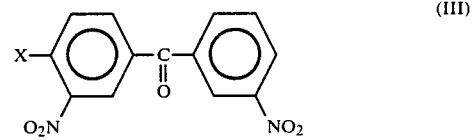

in which X is a halogen atom;

A benzophenone compound of the general formula

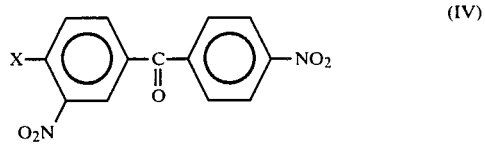

in which X is a halogen atom;

A benzophenone compound of the general formula

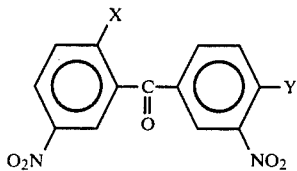

(V)

in which X and Y are the same or different halogen atoms.

More specifically, as 3,3'-dinitro-4,4'-dihalogeno benzophenone expressed by the above formula (II), there can be exemplified such compounds as 3,3'-dinitro-4,4'-dichloro benzophenone, 3,3'-dinitro-4,4'-dibromo benzophenone, 3,3'-dinitro-4,4'-difluoro benzophenone, 3,3'-dinitro-4,4'-diiodo benzophenone, 3,3'-dinitro-4-chloro-4'-bromo benzophenone, 3,3'-dinitro-4-chloro-4'-iodo benzophenone.

As 3,3'-dinitro-4-halogeno benzophenones having the above formula (III), there can be exemplified such compounds as 3,3'-dinitro-4-chloro benzophenone, 3,3'-dinitro-4-bromo benzophenone, 3,3'-dinitro-4-fluoro benzophenone, and 3,3'-dinitro-4-iodo benzophenone.

As 4-halogeno-3,4'-dinitro benzophenone of the above formula (IV), there can be exemplified such ones as 4-chloro-3,4'-dinitro benzophenone, 4-bromo-3,4'-dinitro benzophenone, 4-iodo-3,4'-dinitro benzophenone, and 4-fluoro-3,4'-dinitro benzophenone.

As 2,4'-dihalogeno-5,3'-dinitro benzophenones of the formula (V), there can be exemplified such compounds as 2,4'-dichloro-5,3'-dinitro benzophenone, 2,4'-dibromo-5,3'-dinitro benzophenone, 2,4'-difluoro-5,3'-dinitro benzophenone, 2-chloro-4'-bromo-5,3'-dinitro benzophenone, 2-chloro-4'-fluoro-5,3'-dinitro benzophenone, 2-chloro-4'-iodo-5,3'-dinitro benzophenone, 2-bromo-4'-chloro-5,3'-dinitro benzophenone, 2-bromo-4'-fluoro-5,3'-dinitro benzophenone, 2-fluoro-4'-chloro-5,3'-dinitro benzophenone, 2-fluoro-4'-bromo-5,3'-dinitro benzophenone, 2-iodo-4'-chloro-5,3'-dinitro benzophenone.

It is advantageous from the commercial standpoint to utilize the benzophenones having chlorine atoms as halogens.

The halogeno dinitro benzophenones as exemplified above can be easily prepared by the nitration of the corresponding halogeno benzophenones, respectively, such as 4,4'-dihalogeno benzophenone, 4-halogeno benzophenone, 4-halogeno-4'-nitro benzophenone, or 2,4'-dihalogeno benzophenone. Thus, the nitration of 4,4'-dichloro benzophenone by the mixed acid will produce 3,3'-dinitro-4,4'-dichloro benzophenone, falling within the above formula (II), with a yield of 95-98% (E. R. Kofanov et al., J. Org. Chem. of USSR, 15, 98-100 (1979)). There can be obtained 3,3'-dinitro-4-chloro benzophenone, one of the compounds of the above formula (III), in such a yield as 96-98%, through the nitration of 4-chloro benzophenone by sodium nitrate and concentrated sulfuric acid (G. S. Mironov et al., J. Org. Chem. of USSR, 8, 1538 (1972)). As a further example, 4-halogeno-3,4'-dinitro benzophenone, falling within the above general formula (IV), can be easily obtained by the nitration of 4-halogeno-4'-nitro benzophenone which has been produced through the condensation reaction of p-nitro benzoylchloride and halogeno-benzene (P. J. Montagne et al., Ber., 49, 2267-2270 (1916)), and G. S. Mironov et al., J. Org. Chem. of USSR, 8, 1538-1543 (1972)). There can be prepared a high yield of 2,4'-dihalogeno-5,3'-dinitro benzophenone, a benzophenone of the general formula (V), through the nitration of 2,4'-dihalogeno benzophenone which has been produced by the condensation reaction of 2-halogeno benzoylchloride and halogenobenzene (H. F. Faith et al., J. Am. Chem. Soc., 77, 543 (1955)).

As an alternative method, it is advantageous to prepare 3,3'-dinitro-4,4'-dichloro benzophenone (falling within the general formula (II)) through the nitration of 4,4'-dichloro benzophenone in a fatty halogenated hydrocarbon solvent. As examples of the fatty halogenated hydrocarbon solvents to be used in such a method, there are included dichloro methane, chloroform, carbon tetrachloride, 1,1-dichloro ethane, 1,2-dichloro ethane, 1,1,1-trichloro ethane, 1,1,2-trichloro ethane, 1,1,1,2-tetrachloro ethane, 1,1,2,2-tetrachloro ethane, 1,2-dichloro ethylene, trichloro ethylene and tetrachloro ethylene. While there is no limitation on the amount of the solvent, it is general that the solvent is used 0.2-20 times by weight, preferably 1-10 times by weight, based on the raw material, 4,4'-dichloro benzophenone. In this method there is employed the mixed acid or a nitrate+sulfuric acid as nitrating agent. Nitric acid is used in an amount of 2.0-5.0 times, more preferably 2.2-3.0 times, by mols as much as the amount of the raw material, 4,4'-dichloro benzophenone. While concentration of nitric acid is not critical, it is general to use nitric acid of a specific gravity of 1.30-1.50, more preferably 1.42-1.50. It is preferred to use a nitrate in an amount of 2-3 times in mols, more preferably 2.1-2.5 times in mols, as much as the raw material. As preferred nitrates, there can be exemplified sodium nitrate and potassium nitrate. Sulfuric acid used preferably in an amount of 2-8 times in mols, more preferably 4-6 times in mols as much as the raw material. Concentration of sulfuric acid had best be more than 70%.

This method may be carried out by adding the mixed acid dropwise to 4,4'-dichloro benzophenone dissolved in the organic solvent, or by adding the organic solvent to 4,4'-dichloro benzophenone in the mixed acid. Otherwise, the method may be conducted by adding 4,4'-dichloro benzophenone to a mixture of the mixed acid and the organic solvent. In case where a nitrate is employed in place of nitric acid, it is general that to 4,4'-dichloro benzophenone in the organic solvent there is added nitric acid and then sulfuric acid dropwise. The reaction temperature is in the range of 40°-80° C., preferably 40°-80° C. The reaction is generally completed in 2-10 hours.

After the completion of the reaction, the organic phase is separated from the mixed acid phase. Then, the solvent is distilled out from the organic phase which is then filtered, washed with water and dried to give a high yield and purity of 3,3'-dinitro-4,4'-dichloro benzophenone crystals.

The benzophenone of the above-mentioned general formula (I) to be used in the process of the present invention may be in the form of a mixture of various dinitro-dichloro benzophenones produced by the nitration of a mixture which has been produced by the Friedle-Crafts' reaction of 2-chloro benzoylchloride and/or 4-chloro benzoylchloride with chlorobenzene.

In such a method, firstly Friedle-Crafts' reaction of chlorobenzoylchlorides and chlorobenzene is carried out, which is hereinafter referred to as the first step of the reaction. In the first step reaction, 2-chloro benzoylchloride and/or 4-chloro benzoylchloride are used where the amount of the benzoylchloride(s) is 1.1–3 times in mols as much as chlorobenzene.

Any type of catalyst generally used in Friedle-Crafts' reaction may be applied in the first step of the reaction, representative of such catalyst being anhydrous aluminum chloride, anhydrous ferric chloride, ferric sulfate, and boron trifluoride. Anhydrous ferric chloride is most often used because of low cost and easy handling. The amount of catalyst used is 0.5–10 molar %, preferably 1–5 molar % based on chloro benzoylchlorides.

The first step of reaction proceeds at reflux by excessive chlorobenzene, i.e. at a temperature of 140°–180° C. until the production of hydrochloric acid ceases. Thus, the completion of the reaction may be detected through the determination of the production of hydrochloric acid gas or through the determination of consumption of chloro benzoylchlorides by a suitable means such as gas chromatography or high performance liquid chromatography. After the completion of the reaction, unreacted chlorobenzene is removed out of the reaction system by means of vacuum distillation or steam distillation to obtain a mixture of dichlorobenzophenones.

The mixture of dichlorobenzophenones is then subjected to a nitration reaction to produce dinitro-dichloro-benzophenones, which reaction is referred to as the second step of the reaction. The second step of the reaction can be carried out under the same conditions, regardless of forms of dichloro benzophenones (2,4'-, 4,4'- or 2,2' forms) and the amounts thereof contained in the mixture produced in the first step of reaction. While any type of conventional nitrating agent may be used including the mixed acid, fuming nitric acid and nitric acid+acetic acid, it is general to use the mixed acid or fuming nitric acid. When the nitration is carried out using fuming nitric acid, 80–95% nitric acid is used in an amount of 8–12 times in mols as much as the crude dichlorobenzophenones. When the nitration is carried out using a combination of nitric acid or a nitrate (such as sodium nitrate or potassium nitrate) plus concentrated sulfuric acid, the molar proportion of the crude dichlorobenzophenones:nitric acid or nitrate:concentrated sulfuric acid is in the range of 1:2.1–3.0:4–6. If required, use may be made, in the nitration, of a halogenated hydrocarbon solvent such as methylene chloride, 1,2-dichloro ethane, 1,1,2-trichloro ethane, chloroform, carbon tetrachloride, 1,1,2,2-tetrachloro ethane or trichloro ethane.

The nitration reaction may be carried out by mixing together the crude dichlorobenzophenones, a nitrating agent and, if required, a solvent. However, the nitration may be carried out, particularly in the case where the mixed acid is employed as nitrating agent, by adding the crude dichlorobenzophenones to the mixed acid or by adding nitric acid (or a nitrate) to a mixture of the crude dichlorobenzophenones and sulfuric acid. By heating the crude dichlorobenzophenones and the mixed acid while stirring, the nitration reaction proceeds. Preferably, reaction temperature is in the range of 50°–100° C. and reaction time is in the range of 2–10 hours. The completion of the reaction can be detected by thin layer chromatography or high performance liquid chromatography.

After the completion of the reaction, the desired compounds are separated from the product in any conventional manner: For example, when solvent was not used, the product is diluted with water and then subjected to a filtering. Otherwise, when solvent was used, the solvent phase is separated from the acid phase, and then the solvent is distilled out by steam distillation. The precipitate is filtered to give, as product of the second step of the reaction, a mixture of various types dinitro-dichloro benzophenones such as 5,3'-dinitro-2,4'-dichloro benzophenone, 3,3'-dinitro-4,4'dichlor benzophenone or 5,5'-dinitro-2,2'-dichloro benzophenones.

Such mixture of various dinitro-dichloro benzophenones can be applied, without need of isolating dinitro-dichloro benzophenones from each other, to the subsequent reduction-dechlorination reaction (the third step of reaction) to yield 3,3'-diamino benzophenone.

The third step of reaction may be carried out in the following manner: (A) To the crude dinitro-dichloro benzophenones dissolved or suspended in a solvent there is added a reduction catalyst. Then, the mixture is introduced with hydrogen at a predetermined temperature, while stirring. Dechlorination reaction follows by the addition of a dehydrochlorination agent. Alternatively, (B) a dehydrochlorination agent is added at the time of addition of the reduction catalyst, and then there is introduced hydrogen into the mixture at a predetermined temperature while being stirred, so that reduction reaction of the nitro groups and dechlorination will proceed simultaneously. In both cases, the reaction proceeds smoothly to produce the desired compound, 3,3'-diamino benzophenone. However, because of nucleophilic nature of the chlorine atoms of dinitro-dichloro benzophenones, in the method (B) there may occur some side reactions with dehydrochlorination agent so as to decrease the yield of the desired compound. The method (A) is therefore preferred.

In the preparation of 3,3'- or 3,4'-diamino benzophenone from a benzophenone or benzophenones of the formula (I), there can be used many metal catalysts which have been generally for use in a catalytic reduction. For example, nickel, palladium, rhodium, ruthenium, cobalt or copper may be used as reduction catalyst in the process of the present invention. From commercial standpoint, it is preferably to use a palladium catalyst. While these catalysts may be used in metallic states, it is general that they are supported on carriers such as carbon, barium sulfate, silica gel or alumina. Such metal as nickel, cobalt or copper may be used in the form of a Raney catalyst. The amount of reduction catalyst to be used is in the range of 0.01–10% by weight as metal (generally, 2–8% by weight when used in metallic state, while 0.1–5% by weight when used in the form of supported catalyst) on the basis of the amount of the benzophenone of the formula (I) as raw material.

As dehydrohalogenation agents to be used in the process of the present invention, there can be exemplified oxides, hydroxides, carbonates or bicarbonates of alkaline or alkaline earth metals, ammonia and organic amines. More specifically, such compounds as calcium carbonate, sodium hydroxide, magnesium oxide, ammonium bicarbonate, calcium oxide, lithium hydroxide, barium hydroxide, potassium carbonate, potassium hydroxide, ammonia, triethyl amine, tri-n-butyl amine, triethanol amine, pyridine or N-methyl morpholine. A mixture of two or more of such dehydrohalogenation agents may be used. The amount of dehydrohalogenation agent is generally in the range of 0.5 to 5 times, preferably 1 to 3 times, as much as the benzophenone of (I) as raw material.

The reduction and dehalogenation reaction is generally carried out using a solvent. There is no limitation on the type of solvent to be used unless it is extremely inactive. Thus, there can be used such solvents as alcohols such as methanol, ethanol, or isopropyl alcohol, ethers such as dioxane, tetrahydrofuran or methylcellosolve, fatty hydrocarbons such as hexane or cyclohexane, aromatic hydrocarbon such as benzene, toluene, or xylene, esters such as ethyl acetate or butyl acetate, halogenated hydrocarbons such as dichloro methane, chloroform, carbon tetrachloride, 1,2-dichloro ethane, 1,1,2-trichloro ethane or tetrachloro ethane, N,N-dimethyl formamide or dimethyl sulphoxide. If the reaction rate is slow in the use of a solvent insoluble with water, there may be used a conventional interphase transfer catalyst such as a quarternary ammonium salt or phosphonium salt to accelerate the reaction. The amount of solvent is not limited as long as the benzophenones as raw materials are suspended or dissolved in the solvent. Generally, it is sufficient to use solvent in an amount of 0.5 to 10 times as much as the raw material.

There is no limitation on reaction temperature, and the reaction is generally in the range of 20°–200° C., more preferably in the range of 20°–100° C. Reaction pressure is generally in the range of atmospheric pressure to 50 Kg/cm².G.

The reduction and dehalogenation reaction of the process of the present invention may be generally carried out in the following manners: (A) To the benzophenones of the formula (I) dissolved or suspended in a suitable solvent there is added a reduction catalyst, followed by the introduction of hydrogen while the mixture is being stirred, at a predetermined temperature. Then, a dehydrohalogenation agent is added to conduct dehalogenation reaction. Otherwise, (B) addition of a dehydrohalogenation agent is made together with the addition of a reduction catalyst, and then there is introduced hydrogen with the mixture being stirred, at a predetermined temperature, so that the reduction of the nitro groups and the dehalogenation will occur simultaneously. In both cases, the reaction proceeds smoothly to produce the desired compound, 3,3'- or 3,4'- diamino benzophenone. However, in the latter case, there may be side reactions of benzophenones with the dehydrohalogenation agent because of nucleophilic nature of the halogen atoms on the benzophenones. Therefore, the method (A) is preferred.

The degree of the reaction can be detected by determination of the calculated amount of hydrogen absorbed or by thin layer chromatography. After removal of the catalyst and the inorganic salts by such a procedure as heat filtering or extraction, from the reaction system, concentration procedure is carried out depending upon requirement to give crystals of 3,3'- or 3,4'-diamino benzophenone. Alternatively, dry HCL gas there is introduced to the reaction liquid, out of which the catalyst and the inorganic salts have been separated, to obtain 3,3'- or 3,4'-diamino benzophenone in the form of hydrochloric acid addition salt.

In a known process to reduce a halogen-substituted dinitro benzophenone there is produced 4-halogeno-3,4'-diamino benzophenone or 3,4'-diamino benzhydrol (P. J. Montagne et al., Ber., 49, 2268-2271 (1916)). Thus, in the known process for the reduction of a halogeno-dinitro benzophenone, in addition to reduction of the nitro groups to amino groups and, depending upon reaction conditions and the type of reduction catalyst used, dehalogenation, there occurs further reduction by which even the carbonyl group of the benzophenone is converted to produce a benzhydrol compound. By contrast, the present invention provides a novel process for reduction of halogeno-dinitro benzophenones where there occurs only the reduction of the nitro groups to amino groups and the dehalogenation, without causing the reduction of the carbonyl group, thereby to selectively produce 3,3'- or 3,4'-diamino benzophenone. Thus, according to the present invention there is provided a novel process for commercially producing 3,3'- or 3,4'-diamino benzophenone.

The process of the present invention will be more illustrated by the following examples.

EXAMPLE 1

50.2 g (0.2 moles) of 4,4'-dichloro benzophenone is dissolved in 100 ml of 1,2-dichloro ethane. Following addition of 28.2 g of nitric acid (specific gravity 1.50) at room temperature, to the resultant mixture there is added 117 g of 98% sulfuric acid dropwise during 30 minutes at 30°–40° C. After stirring for 8 hours at 70°–80° C., the mixture is cooled and then separated into an organic layer and a mixed acid layer. The organic layer is washed with 100 ml of water and the solvent is removed by steam distillation. The precipitate is filtered, washed with water and dried to give slightly yellow prism-like crystals of 3,3'-dinitro-4,4'-dichloro benzophenone (68.2 g). Yield 99%. Purity determined by high performance liquid chromatography is 99.7%. Melting point 131°–132.5° C. By recrystallization from ethanol there is obtained slightly yellow prism-like pure crystals. M.P. 132.5° C.

Elemental Analysis:

|  | C | H | N | Cl |
| --- | --- | --- | --- | --- |
| Calc. (%) | 45.76 | 1.76 | 8.21 | 20.80 |
| Found (%) | 45.80 | 1.78 | 8.25 | 20.82 |

EXAMPLE 2

50.2 g (0.2 moles) of 4,4'-dichloro benzophenone is added with 117 g of 98% sulfuric acid and then 100 ml of 1,1,1-trichloro ethane. After the resultant mixture is added dropwise with 53.7 g of nitric acid (specific gravity 1.42), it is stirred for 10 hours at 70°–80° C. and then cooled to be separated into an organic layer and a mixed-acid layer. After removal of the solvent by steam distillation, the precipitate is filtered, washed with water and dried to obtain slightly yellow prism crystals of 3,3'-dinitro-4,4'-dichloro benzophenone (68.2 g). Yield 99%. Purity is found to be 99.5% by high performance liquid chromatography. M.P. 131°–132.5° C.

EXAMPLE 3

To 50.2 g (0.2 moles) of 4,4'-dichloro benzophenone dissolved in 100 ml of 1,2-dichloro ethane, there is added 37.4 g of sodium nitrate and then 120 g of 98% sulfuric acid dropwise during 30 minutes at 30°–40° C. After the mixture is stirred for 8 hours at 70°–80° C., it is cooled and added with 40 ml of water to dissolve sodium nitrate. The mixture is separated into an organic layer and a mixed-acid layer and the organic layer is washed with 100 ml of water. After the solvent is removed by steam distillation, the precipitate is filtered, washed with water and dried to give slightly yellow prism-like crystals of 3,3'-dinitro-4,4'-dichloro benzophenone 66.8 g. Yield 98%. Purity is found to be 99.7%. M.P. 131°–132.5° C.

EXAMPLE 4 AND 5

The same procedures were made as in Example 1 except that the types and the amounts of solvent and the amounts of nitric acid and sulfuric acid were changed as given in Table I, to obtain the desired products. The results are summarized in Table I.

EXAMPLE 7

To a closed glass vessel equipped with a thermometer and a stirrer, there are added 102 g (0.3 moles) of 3,3'-dinitro-4,4'-dichloro benzophenone, 5 g of 5% palladium/active carbon catalyst (available from Nihon Engelhardt Co.) and 300 ml of dioxane. While the mixture is being stirred at 70°–80° C., hydrogen is introduced in the vessel so that 41.5 l (1.85 moles) of hydrogen is absorbed into the mixture over 8 hours. After addition of 80 g (0.8 moles) of 40% aqueous sodium hydroxide, hydrogen is again introduced to the vessel with the mixture being stirred at 70°–80° C., so that it is absorbed 13.8 l (0.62 moles) over 3 hours. The reaction solution is filtered at 70°–80° C. to remove the catalyst. On cooling the solution, there is obtained 3,3'-diamino benzophenone, as yellow needle-like crystals. The crystals are filtered, washed with 30 ml of 50% aqueous solution of dioxane and dried. Yield 59.2 g (93%). M.P. 149°–151° C.

TABLE I

| Example No. | Starting Material (g) | | Solvent (ml) | | Nitric Acid g (S.G.) | Sulfuric Acid g | Reaction temp. (°C.) | Reaction time (hr) | Product | Yield (%) | Purity (%) |
|---|---|---|---|---|---|---|---|---|---|---|---|
| 1 | 4,4'-dichloro benzophenone | 50.2 | 1,2-dichloro ethane | 100 | 28.2 (1.50) | 117 | 70–80 | 8 | 3,3'-dinitro-4,4'-dichloro benzophenone | 99 | 99.7 |
| 2 | 4,4'-dichloro benzophenone | 50.2 | 1,1,1-trichloro ethane | 100 | 53.7 (1.42) | 117 | 70–80 | 10 | 3,3'-dinitro-4,4'-dichloro benzophenone | 99 | 99.5 |
| 3 | 4,4'-dichloro benzophenone | 50.2 | 1,2-dichloro ethane | 100 | NaNO$_3$ 37.4 | 120 | 70–80 | 8 | 3,3'-dinitro-4,4'-dichloro benzophenone | 98 | 99.7 |
| 4 | 4,4'-dichloro benzophenone | 50.2 | dichloro methane | 200 | 28.2 (1.50) | 84 | 40–45 | 2 | 3,3'-dinitro-4,4'-dichloro benzophenone | 99 | 99.9 |
| 5 | 4,4'-dichloro benzophenone | 50.2 | tetrachloro ethylene | 200 | 28.2 (1.50) | 100 | 70–80 | 4 | 3,3'-dinitro-4,4'-dichloro benzophenone | 99 | 99.5 |

EXAMPLE 6

To an autoclave there are added 50 g (0.15 moles) of 3,3'-dinitro-4,4'-dichloro benzophenone, 21 g (0.38 moles) of calcium oxide, 1 g of 5% palladium/alumina catalyst (available from Nihon-Engelhardt Co., Ltd.) and 350 ml of 1,2-dichloro ethane. The reaction is carried out for ten hours by introducing hydrogen into the autoclave, with the mixture being stirred at 30°–35° C., to keep the pressure at 10 Kg/cm$^2$.G. After the completion of the reaction, the reaction mixture is heated up to 70° C. and subjected to a hot filtering so as to remove the catalyst and the inorganic salt. On cooling the mixture there are obtained yellow needle-like crystals of 3,3'-diamino benzophenone. The crystals are filtered, washed with 10 ml of 1,2-dichloro ethane and dried. Yield 21.2 g (67%). M.P. 149°–150.5° C. Recrystallization from ethanol gives pure crystals. M.P. 150°–151° C.

Elemental Analysis:

|  | C | H | N |
|---|---|---|---|
| Calc. (%) | 73.5 | 5.7 | 13.2 |
| Found (%) | 73.4 | 6.0 | 12.7 |

EXAMPLES 8–16

The procedures as in Example 7 are repeated, by varying 3,3'-dinitro-4,4'-dihalogeno benzophenones as starting materials, catalysts and amounts thereof, solvents and amounts thereof, dehydrohalogenation agents and amounts thereof, temperatures and pressures. The results are shown in Table II.

TABLE II

| | Feed Materials $\mathrm{X-\bigcirc-\overset{O}{\underset{\|}{C}}-\bigcirc-Y}$ with $O_2N$ | | | | | | Dehydro-halogenation agent (mole) | Reaction Conditions | | | Yield (%) |
|---|---|---|---|---|---|---|---|---|---|---|---|
| Example No. | X | Y | NO$_2$ (mole) | Catalyst (g) | | Solvent (ml) | | Temp. (°C.) | Pressure Kg/cm$^2$ · G | Time (hr) | |
| 8 | Cl | Cl | 0.3 | 5% Pd/C | 5 | Dioxane | 300 | 40% Aqueous NaOH Solution 0.8 | 70–80 | Atm. Pre. | 11 | 93 |
| 9 | F | F | 0.3 | 5% Pt/C | 5 | Ethanol | 250 | Triethanol amine 0.75 | 60–70 | Atm. Pre. | 17.5 | 83 |
| 10 | Br | Cl | 0.1 | 2% Pd/C | 5 | Ethyl acetate | 150 | Ca(OH)$_2$ 0.9 | 40–50 | Atm. Pre. | 19 | 88 |
| 11 | Cl | Cl | 0.3 | Raney nickel | 8 | Dioxane | 300 | Triethyl amine 0.75 | 25–35 | 2–3 | 28 | 76 |
| 12 | Br | Br | 0.3 | 5% Rh/C | 5 | DMF | 200 | 15% Aqueous | 80–100 | Atm. | 22 | 83 |

TABLE II-continued

| | Feed Materials | | | | | | | Dehydro-halogenation agent (mole) | Reaction Conditions | | | Yield (%) |
|---|---|---|---|---|---|---|---|---|---|---|---|---|
| Example No. | X | Y | O₂N, NO₂ (mole) | Catalyst (g) | | Solvent (ml) | | | Temp. (°C.) | Pressure Kg/cm²·G | Time (hr) | |
| 13 | Cl | Cl | 0.3 | 2% Pd/C | 7 | Dioxane | 300 | NaOH Solution 0.8 30% Ammonia Water 0.75 | 80–90 | Pre. 5–7 | 13.5 | 92 |
| 14 | Cl | I | 0.3 | 5% Pd/C | 5 | Ethylene glycol | 250 | Magnesium Oxide 0.9 | 80–100 | Atm. Pre. | 15 | 88 |
| 15 | Cl | Cl | 0.3 | 1% Pd/C | 10 | Dioxane | 300 | 50% Aqueous KOH Solution 0.6 | 70–80 | Atm. Pre. | 26 | 91 |
| 16 | F | F | 0.3 | 5% Pd/C | 5 | Ethanol | 230 | Sodium bicarbonate 0.9 | 60–70 | 2–3 | 9 | 85 |

EXAMPLE 17

To a closed glass vessel equipped with a thermometer and a stirrer, there are added 49 g (0.15 moles) of 3,3'-dinitro-4-chloro-4'-fluoro benzophenone, 1 g of palladium black catalyst and 300 ml of benzene. While the mixture being stirred at 65°–70° C., 20.2 l (0.9 moles) of hydrogen is absorbed therein during about 6 hours. Then, after there are added 180 g (0.45 moles) of 35% aqueous solution of potassium carbonate and 3 g of 90% aqueous solution of trioctylmethyl ammonium chloride (available from Tokyo-Kasei Co.), additional hydrogen, 7.4 l (0.33 moles), is introduced during about 5 hours while the mixture being stirred at 65°–70° C. The mixture at that temperature is filtered to remove the catalyst. Organic phase is separated from the filtrate, added with magnesium sulfate for removing water and then blown with dry hydrochloric gas to saturation. The precipitate thus obtained is filtered, washed with 50 ml of benzene and dried to obtain 33.2 g (yield 77.7%) of 3,3'-diamino benzophenone in the hydrochloric acid salt form. Recrystallization from 20% aqueous isopropyl alcohol gives pure compound, as slightly yellow needle-like crystals. M.P. 265°–267° C. (decomposed).

Elemental Analysis:

| | C | H | N | Cl |
|---|---|---|---|---|
| Calc. (%) | 54.7 | 4.9 | 9.8 | 24.9 |
| Found (%) | 54.2 | 5.1 | 9.7 | 25.1 |

EXAMPLE 18

To a closed glass vessel equipped with a thermometer and a stirrer, there are charged 105.3 g (0.3 moles) of 3,3'-dinitro-4-bromo benzophenone, 5 g of 5% palladium/active carbon catalyst (available from Nihon-Engelhardt Co.) and 300 ml of dioxane. With the mixture being stirred at 70°–80° C., hydrogen is introduced into the vessel so that 40.5 l (1.81 moles) of hydrogen is absorbed in the mixture over about 8 hours. Then, after 33 g (0.33 moles) of 40% aqueous solution of caustic soda is added, hydrogen is further introduced at 70°–80° C. with the mixture being stirred so that an additional 7.2 l (0.32 moles) is absorbed during three hours. The reaction liquid is filtered at 70°–80° C. so as to remove the catalyst and then allowed to cool giving yellow needle-like crystals of 3,3'-diamino benzophenone. The crystals is filtered, washed with 30 ml of 50% aqueous solution of dioxane, and dried. Yield 93% (59.2 g). M.P. 149°–150° C.

EXAMPLES 19-24

The same procedures as in Example 18 are repeated except that the types of 3,3'-dinitro-4-halogeno benzophenone, the types of catalyst and amounts thereof, type of solvents and amounts thereof, reaction temperatures and pressures are changed as given in Table III in which the results of the respective reactions are also set forth.

TABLE III

| | Feed Materials | | | | | | Dehydro-halogenation agent | (mole) | Reaction Conditions | | | Yield (%) |
|---|---|---|---|---|---|---|---|---|---|---|---|---|
| Example No. | X | O₂N, NO₂ (mole) | Catalyst (g) | | Solvent (ml) | | | | Temp. (°C.) | Pressure Kg/cm²·G | Time (hr) | |
| 18 | Br | 0.3 | 5% Pd/C | 5 | Dioxane | 300 | 40% Aqueous NaOH Solution | 0.33 | 70–80 | Atm. Pre. | 11 | 93 |
| 19 | F | 0.3 | 5% Pt/C | 5 | Ethanol | 250 | Sodium carbonate | 0.45 | 60–70 | 8–10 | 9 | 89 |
| 20 | I | 0.1 | 5% Pd/C | 3 | Ethyl acetate | 150 | Magnesium hydroxide | 0.15 | 40–50 | Atm. Pre. | 16 | 90 |
| 21 | Cl | 0.3 | Raney nickel | 8 | Dioxane | 300 | Triethyl amine | 0.39 | 25–35 | 3–5 | 26 | 82 |
| 22 | Cl | 0.3 | 5% Rh/C | 5 | DMF | 200 | 50% Aqueous KOH Solution | 0.33 | 80–90 | Atm. Pre. | 18 | 85 |

TABLE III-continued

| | Feed Materials $X-\bigcirc-\underset{O}{\overset{\|}{C}}-\bigcirc$ $O_2N \qquad NO_2$ | | | | | Dehydro- halogenation agent | Reaction Conditions | | | |
|---|---|---|---|---|---|---|---|---|---|---|
| Example No. | X | (mole) | Catalyst (g) | Solvent (ml) | | (mole) | Temp. (°C.) | Pressure Kg/cm$^2$ · G | Time (hr) | Yield (%) |
| 23 | Cl | 0.3 | 5% Pd/C | 3 | Dioxane | 300 | 30% Ammonia Water | 0.45 | 80–90 | 5–7 | 9 | 92 |
| 24 | Cl | 0.3 | 5% Pd/C | 5 | Methyl cellosolve | 300 | Triethanol amine | 0.39 | 80–100 | Atm. Pre. | 10 | 92 |

EXAMPLE 25

To a closed glass vessel equipped with a thermometer and a stirrer, there are added 46 g (0.15 moles) of 3,3'-dinitro-4-chloro benzophenones, 1 g of palladium black catalyst and 300 ml of benzene. While the mixture being stirred at 65°–70° C., hydrogen is introduced so that 20.2 l (0.9 moles) of hydrogen is absorbed into the mixture during about 6 hours. 79 g (0.2 moles) of 35% aqueous solution of potassium carbonate and 3 g of 90% aqueous solution of trioctyl methyl ammonium chloride (from Tokyo-Kasei Co., Japan) are added and then an additional amount of hydrogen, 3.4 l (0.15 moles), is introduced during about 3 hours while the mixture being stirred at 65°–70° C. The reaction solution is filtered at that temperature to remove the catalyst and the organic phase is separated. After there is added magnesium sulfate to the organic phase for water-removal, dry hydrochloric gas is blown into the phase to saturation. The precipitate thus formed is filtered, washed with 50 ml of benzene, and dried to give hydrochloric acid addition salt form of 3,3'-diamino benzophenone crystals. Yield 31.9 g (74.6%). Recrystallization from 20% hydrous isopropanol gives pure compound, as slightly yellow needle-like crystals. M.P. 267° C. (decomposed).
Elemental Analysis:

| | C | H | N | Cl |
|---|---|---|---|---|
| Calc. (%) | 54.7 | 4.9 | 9.8 | 24.9 |
| Found (%) | 54.0 | 5.2 | 9.6 | 24.7 |

EXAMPLE 26

In an autoclave, there are charged 46 g (0.15 moles) of 3,3'-dinitro-4-chloro benzophenone, 11.2 g (0.2 moles) of calcium oxide, 1 g of 5% palladium/alumina catalyst (available from Nihon-Engelhardt Co.) and 250 ml of 1,2-dichloro ethane. With the mixture being stirred at a temperature of 30°–35° C., the reaction proceeds by the introduction of hydrogen for seven hours under a constant pressure of 10 Kg/cm$^2$.G. After completion of the reaction, the reaction mixture is heated up to 70° C. for hot-filtering so as to remove the catalyst and the inorganic salt. On cooling, there is obtained 3,3'-diamino benzophenone as yellow needle-like crystals. The crystals are filtered, washed with 20 ml of 1,2-dichloro ethane and dried. Yield 24.8 g (78%). M.P. 149°–150° C. Recrystallization from ethanol gives yellow needle-like pure crystals of the benzophenone. M.P. 150°–151° C.
Elemental Analysis:

| | C | H | N |
|---|---|---|---|
| Calc. (%) | 73.5 | 5.7 | 13.2 |
| Found (%) | 72.9 | 6.2 | 13.1 |

EXAMPLE 27

In a closed vessel equipped with a thermometer and a stirrer there are charged 105 g (0.3 moles) of 4-bromo-3,4'-dinitro benzophenone, 5 g of 5% palladium/active carbon catalyst (from Nihon-Engelhardt Co.) and 300 ml of dioxane. At 70°–80° C., with the mixture being stirred, there is introduced 41 l (1.83 moles) of hydrogen so as to be absorbed in the mixture in about 11 hours. Following cooling the mixture to 30° C., there is added 38.5 g (0.33 moles) of 30% ammonia water. Then, again with the mixture being stirred, at 30°–40° C., there is introduced an additional amount of hydrogen, 7.2 l (0.32 moles), during seven hours. The reaction liquid is filtered at 30°–40° C. to remove the catalyst and then allowed to cool giving yellow crystals of 3,4'-diamino benzophenone. The crystals are filtered, washed with 30 ml of 50% aqueous dioxane solution and dried. Yield 58 g (91%). M.P. 121°–123° C.
Elemental Analysis:

| | C | H | N |
|---|---|---|---|
| Calc. (%) | 73.5 | 5.7 | 13.2 |
| Found (%) | 73.1 | 6.0 | 13.1 |

EXAMPLES 28-33

The procedures as made in Example 27 are repeated by varying the type of 4-halogeno-3,4'-dinitro benzophenone, the type and the amount of solvent, the type and amount of dehydrohalogenation agent, reaction temperature and reaction pressure. The results are summarized in Table IV.

TABLE IV

| | Feed Materials | | | | | Dehydro-halogenation agent (mole) | Reaction Conditions | | | Yield (%) |
|---|---|---|---|---|---|---|---|---|---|---|
| Example No. | $O_2N$—X | (mole) | Catalyst (g) | Solvent | (ml) | | Temp. (°C.) | Pressure Kg/cm²·G | Time (hr) | |
| 27 | Br | 0.3 | 5% Pd/C 5 | Dioxane | 300 | 30% Ammonia water 0.33 | (70–80 / 30–40) | Atm. Pre. | 18 | 91 |
| 28 | F | 0.3 | 5% Pt/C 5 | Ethanol | 250 | Calcium oxide 0.3 | 60–70 | Atm. Pre. | 27 | 82 |
| 29 | I | 0.1 | 5% Pd/C 3 | Ethyl acetate | 150 | Magnesium hydroxide 0.15 | 40–60 | Atm. Pre. | 12 | 89 |
| 30 | Cl | 0.3 | Raney nickel 8 | Dioxane | 300 | Triethyl amine 0.39 | (80–100 / 25–30) | 3–5 | 18 | 85 |
| 31 | Cl | 0.3 | 5% Rh/C 5 | DMF | 200 | 30% Aqueous NaOH Solution 0.33 | 40–60 | Atm. Pre. | 38 | 85 |
| 32 | Cl | 0.3 | 5% Pd/C 3 | Dioxane | 300 | 20% Aqueous $Na_2CO_3$ Solution 0.4 | 40–60 | 5–7 | 19 | 92 |
| 33 | Cl | 0.3 | 5% Pd/C 5 | Methyl cellosolve | 300 | Triethanol amine 0.39 | (80–100 / 30–40) | Atm. Pre. | 10 | 93 |

Feed material structure: X—C₆H₄(O₂N)—C(=O)—C₆H₄—NO₂

EXAMPLE 34

In a closed glass vessel equipped with a thermometer and a stirrer there are charged 30.7 g (0.1 moles) of 4-chloro-3,4'-dinitro benzophenone, 1 g of palladium black catalyst and 300 ml of benzene. While the mixture being stirred, at 65°–70° C., hydrogen is introduced so that 13.3 l (0.59 moles) of hydrogen is absorbed in the mixture during about nine hours. After there are added 45 g (0.12 moles) of 15% aqueous solution of sodium hydroxide and 2 g of 90% aqueous solution of trioctyl methyl ammonium chloride (available from Tokyo-Kasei Co.), hydrogen is again introduced so that 2.35 l (0.105 moles) is absorbed during about six hours, while the mixture being stirred at 65°–70° C. The reaction mixture is filtered to remove the catalyst and organic layer is separated. The organic layer is added with magnesium sulfate for water removal and then blown with hydrochloric gas to saturation therewith. The precipitate thus formed is filtered, washed with 50 ml of benzene, and dried to obtain hydrochloric acid salt form of 3,4'-diamino benzophenone. Yield 23.4 g (82%). Recrystallization from 20% aqueous isopropanol gives yellow needle-like pure crystals of the benzophenone. M.P. is 250° C. or higher.

Elemental Analysis:

| | C | H | N | Cl |
|---|---|---|---|---|
| Calc. (%) | 54.7 | 4.9 | 9.8 | 24.9 |
| Found (%) | 54.3 | 5.4 | 9.7 | 24.8 |

EXAMPLE 35

To an autoclave there are added 30.7 g (0.1 moles) of 4-chloro-3,4'-dinitro benzophenone, 10.6 g (0.1 moles) of sodium carbonate, 1 g of 5% palladium/alumina catalyst (available from Nihon-Engelhardt Co.) and 250 ml of 1,2-dichloro ethane. With the mixture being stirred at 30°–35° C., the reaction is carried out at a constant pressure for 10 hours by introducing hydrogen into the mixture. After completion of the reaction, the reaction mixture is heated up to 70° C. to be subjected to filtering for removing the catalyst. Then, on cooling, there is obtained 3,4'-diamino benzophenone in the form of yellow needle-like crystals. The crystals are filtered, washed with 20 ml of 1,2-dichloro ethane and dried. Yield 17.6 g (83%). M.P. 121°–122° C. Recrystallization from ethanol gives yellow needle-like pure crystals of said benzophenone. M.P. 122°–122.5° C.

EXAMPLE 36

In a closed glass vessel with a thermometer and a stirrer, there are charged 102.3 g (0.3 moles) of 2,4'-dichloro-5,3'-dinitro benzophenone, 5 g of 5% palladium/active carbon catalyst (from Nihon-Engelhardt Co.) and 300 ml of dioxane. At 70°–80° C., hydrogen is introduced into the vessel while the mixture being stirred, so that 42 l (1.88 moles) of hydrogen is absorbed in the mixture during ten hours. After being cooled to 30° C., the mixture is added with 55 g (0.9 moles) of 28% ammonia water and then introduced with hydrogen while being stirred at 30°–40° C. so as to absorb 13.2 l (0.59 moles) of hydrogen during 5 hours. The reaction mixture is subject to filtering at 30°–40° C. to remove the catalyst. On cooling, there is obtained 3,3'-diamino benzophenone as yellow crystals. The crystals are filtered, washed with 30 ml of 50% aqueous solution of dioxane and dried. Yield 56.5 g (89%). M.P. 149°–150.5° C. Recrystallization from ethanol gives yellow needle-like pure crystals of said benzophenone. M.P. 150°–151° C.

Elemental Analysis:

| | C | H | N |
|---|---|---|---|
| Calc. (%) | 73.5 | 5.7 | 13.2 |
| Found (%) | 73.3 | 6.0 | 13.1 |

EXAMPLE 37

In a closed glass vessel there are charged 38.6 g (0.1 moles) of 2-chloro-4'-bromo-5,3'-dinitro benzophenone, 1 g of palladium black catalyst and 300 ml of benzene. While the mixture being stirred at 65°–70° C., hydrogen is introduced into the vessel so that 13.8 l (0.62 moles) of hydrogen is absorbed in the mixture during 8 hours. Then, there are added 90 g (0.24 moles) of 15% aqueous solution of NaOH and 2 g of 90% aqueous solution of trioctyl methyl ammonium chloride, and then, there is introduced again hydrogen, while the mixture is being stirred at a temperature of 65°–70° C., so that 4.5 l (0.2 moles) of hydrogen is absorbed during about 5 hours. By filtering the reaction liquid at 65°–70° C. the catalyst is removed, and organic phase is separated from the filtrate. After the organic phase is added with magnesium sulfate for water removal, it is introduced with dry hydrochloric gas until saturated with the gas. The crystals thus formed are filtered, washed with 50 ml of benzene and dried to give 3,3'-diamino benzophenone in the form of hydrochloric acid salt. Yield 21.7 g (76%). Recrystallization from 20% aqueous isopropanol yield slightly yellow needle-like pure crystals of the benzophenone. M.P. 267° C. (decomposed).

Elemental Analysis:

|         | C    | H   | N   | Cl   |
|---------|------|-----|-----|------|
| Cal. (%)  | 54.7 | 4.9 | 9.8 | 24.9 |
| Found (%) | 54.2 | 5.0 | 9.7 | 24.6 |

EXAMPLE 38

In an autoclave there are added 32.5 g (0.1 moles) of 2-chloro-4'-fluoro-5,3'-dinitro benzophenone, 15.9 g (0.15 moles) of sodium carbonate, 2 g of 5% palladium/alumina catalyst (from Nihon-Engelhardt Co.) and 100 ml of ethanol. With the mixture being stirred at 30°–35° C., there is introduced hydrogen into the autoclave, at a constant pressure of 10 Kg/cm$^2$. G, to carry out the reaction for ten hours. After the completion of the reaction, the reaction mixture is heated up to filter out the catalyst and the inorganic salt. Then, on cooling the mixture there is obtained 3,3'-diamino benzophenone in the form of yellow needle-like crystals. The crystals are filtered, washed with 10 ml of ethanol and dried. Yield 16.2 g (76.3%). M.P. 149°–151° C.

EXAMPLE 39

The same procedure as in Example 36 was made except that as starting material there is used 115.7 g (0.3 moles) of 2-bromo-4'-chloro-5,3'-dinitro benzophenone. As a result, there is obtained 57.9 g (91%) of 3,3'-diamino benzophenone.

EXAMPLE 40

The same procedure as in Example 36 is done except that there are used 129.8 g (0.3 moles) of 2-iodo-4'-chloro-5,3'-dinitro benzophenone as starting material and 72.9 g (0.72 moles) of triethyl amine as dehydrohalogenation agent. Yield of 3,3'-diamino benzophenone is 54.9 g (86.2%).

EXAMPLE 41

To a mixture of 175 g (1 mole) of 4-chloro benzoylchloride and 135 g (1.2 moles) of chlorobenzene, there is added 3 g of anhydrous ferric chloride. The reaction is then carried out, under passage of nitrogen gas, at 140°–150° C. for 48 hours, with the reaction mixture being stirred. After completion of reaction, the reaction mixture is cooled down to 90° C., and then added with 200 ml of hot water. Thus, steam distillation is conducted to remove excessive chlorobenzene for recovery. The reaction mixture is then cooled, filtered and dried to yield 235 g (overall yield 94%) of crude dichloro benzophenones in the form of brown particles.

Then the crude dichloro benzophenones are subjected to nitration reaction using 460 g (4.6 moles) of concentrated sulfuric acid and 270 g (3 moles) of 70% nitric acid at 70°–80° C. for 3 hours. After completion of the reaction, the reaction mixture is placed in ice water, filtered, washed with water and dried to yield crude dinitro-dichloro benzophenones in yellowish-brown particles, 310 g (overall yield 91%). Analysis of this product by means of high performance liquid chromatography shows as follows:

5,3'(3,3')-dinitro-2,4'-dichloro benzophenone: 86%
3,3'(3,5')-dinitro-2,2'-dichloro benzophenone: 7.7%
Unidentified: 6.3%

Then, in a closed glass vessel equipped with a thermometer and a stirrer, there are charged 34 g (0.1 moles) of said crude dinitro-dichloro benzophenone, 1 g of 5% Pd/C (from Nihon-Engelhardt Co.) and 100 ml of dioxane. While the mixture being stirred at 70°–80° C., hydrogen is introduced into the vessel so that 14.2 l (0.63 moles) of hydrogen is absorbed during 15 hours. After being cooled to 30° C., the mixture is added with 18.2 g (0.3 moles) of ammonia water and then again introduced, while being stirred at 30°–35° C., with hydrogen so as to absorb 4.3 l (0.19 moles) of hydrogen during 8 hours. After completion of reaction, the mixture is heated up to 70° C. for filtering in order to remove the catalyst. On cooling the mixture, there is obtained 3,3'-diamino benzophenone in yellow crystals. The crystals is filtered, washed with 10 ml of 50% aqueous solution of dioxane and dried. Yield 17.6 g (83.0%). M.P. 148.5°–150° C. Recrystallization from ethanol yields slightly yellow needle-like crystals of said diamino benzophenone. M.P. 150°–151° C.

Elemental Analysis:

|         | C    | H   | N    |
|---------|------|-----|------|
| Calc. (%) | 73.5 | 5.7 | 13.2 |
| Found (%) | 73.3 | 5.8 | 13.1 |

EXAMPLE 42

To a mixture of 175 g (1 mole) of 2-chloro benzoylchloride and 135 g (1.2 moles) of chlorobenzene there is added 3 g of anhydrous ferric chloride. Thus, the reaction is carried out, under the passage of nitrogen gas, at 140°–150° C. for 15 hours, while the mixture being stirred. After completion of the reaction, excessive chlorobenzene is distilled out in vacuo at 140°–150° C. On cooling to room temperature, there are obtained crude dichloro benzophenones in brown oily form, 240 g (overall yield 96%).

The crude dichloro benzophenones are added with 500 ml of 1,2-dichloro ethane, and further 700 g (10 moles) of 90% nitric acid. Thus, the mixture is subjected to reaction at 70°–75° C. for 10 hours, while being stirred. Immediately after the reaction completes, the reaction mixture is cooled to separate out the mixed acid phase. The organic phase is blown with steam to distill out the solvent. Thus there are obtained brown particles, which are filtered, washed with water and dried to give 314 g (overall yield 92.4%) of crude dinitro-dichloro benzophenones (a mixture of dinitro-dichloro benzophenones). Analysis of the crude by means of high performance liquid chromatography shows as follows:

5,3'(3,3')-dinitro-2,4'-dichloro benzophenone: 86%
3,3'(3,5')-dinitro-2,3'-dichloro benzophenone: 7.7%
Unidentified: 6.3%

Then, in a closed glass vessel with a thermometer and a stirrer, there are charged 34 g (0.1 moles) of said crude dinitro-dichloro benzophenone, 1 g of 5% Pd/C and 100 ml of methyl cellosolve. While stirring the mixture, at 40°–50° C., there is introduced hydrogen so that 13.9 l (0.62 moles) of hydrogen is absorbed in the mixture during twelve hours. Then, the mixture is cooled down to 30° C. and added with 18.2 g (0.3 moles) of 28% ammonia water. There is introduced hydrogen, with the mixture being stirred at 30°–35° C., so that 4.3 l (0.19 moles) of hydrogen is absorbed during five hours. After completion of reaction, the mixture is heated up to 70° C. for hot filtering to remove the catalyst. After being added with 100 ml of hot water, the filtrate is allowed to cool to give yellow crystals of 3,3'-diamino benzophenone. The crystals are filtered, washed with 10 ml of ethanol and dried. Yield 16.8 g (79.2%). M.P. 148°–150° C. Recrystallization from ethanol yields slightly yellow needle-like crystals of the diamino benzophenone. M.P. 150° to 151° C.

Elemental Analysis:

|  | C | H | N |
|---|---|---|---|
| Calc. (%) | 73.5 | 5.7 | 13.2 |
| Found (%) | 73.5 | 5.8 | 13.1 |

EXAMPLE 43

In a closed glass vessel equipped with a thermometer and a stirrer, there are charged 34 g (0.1 moles) of the crude dinitro-dichloro benzophenones as obtained in Example 41, 0.5 g of 5% Pd/C catalyst and ethanol. Into the mixture there is introduced hydrogen, with the mixture being stirred at 20°–25° C., so that 14 l (0.63 moles) of hydrogen is absorbed in the mixture. Being maintained at that temperature, the mixture is added with 32.8 g (0.22 moles) of triethanol amine and then introduced with hydrogen to absorb 4.4 l (0.2 moles) of hydrogen during 5 hours. After completion of the reaction, the mixture is heated to 70° C. and then subjected to hot filtering in order to the catalyst. On cooling the filtrate, there is obtained 3,3'-diamino benzophenone, yellow needle-like crystals. The crystals are filtered, washed with 10 ml of ethanol, washed with water and dried. Yield 18.3 g (86.2%).

EXAMPLE 44

The same procedure as in Example 43 is made, except that the dehydrohalogenation agent is replaced with 60 g (0.3 moles) of 20% aqueous solution of sodium hydroxide. There is obtained 17.4 g (82.2%) of 3,3'-diamino benzophenone.

EXAMPLE 45

In an autoclave there are charged 34 g (0.1 moles) of the crude dinitro-dichloro benzophenone, 1 g of palladium black catalyst, 8 g (0.2 moles) of magnesium oxide and 200 ml of benzene. While stirring the resultant mixture at 30°–35° C., hydrogen is introduced into the vessel under a constant pressure of 10 Kg/cm$^2$.G to carry out the reaction for 13 hours. After completion of the reaction, the mixture is heated to 70° C. and subjected to hot filtering to remove the catalyst and the inorganic salt. On cooling the filtrate, there is obtained 3,3'-diamino benzophenone in the form of yellow needle-like crystals. The crystals are filtered, washed with 10 ml of methanol and dried. Yield 14.4 g (68%).

What is claimed is:

1. A process for preparing 3,3'- or 3,4'-diamino benzophenone which comprises catalytically reducing and dehalogenating, in the presence of a reduction catalyst and a dehydrohalogenation agent, a benzophenone compound or benzophenone compounds of the following general formula

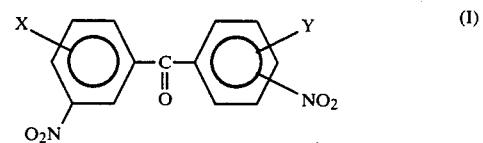

in which X is a halogen atom at position 2 or 4 of the benzene ring and Y is hydrogen or a halogen atom and in which the nitro group is at position 3' or 4' of the benzene ring if Y is hydrogen, while Y is at position 4' and the nitro group is at position 3' if Y is a halogen atom.

2. The method according to claim 1 in which the benzophenone compound or compounds of the general formula (I) have the following general formula

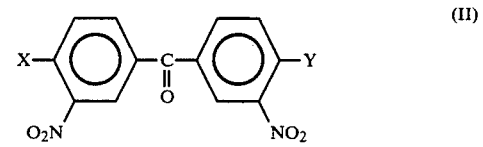

in which X and Y are the same or different halogen atoms.

3. The process according to claim 1 in which the benzophenone compound or compounds of the general formula (I) have the following general formula

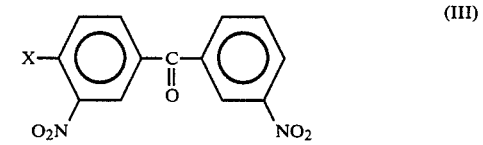

in which X is a halogen atom.

4. The process according to claim 1 in which the benzophenone compound or compounds of the general formula (I) have the following general formula

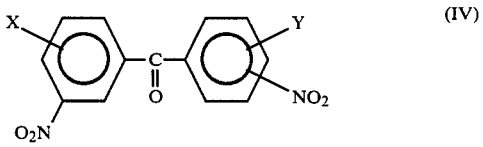

in which X is a halogen atom.

5. The process according to claim 1 in which the benzophenone compound or compounds of the general formula (I) have the following general formula

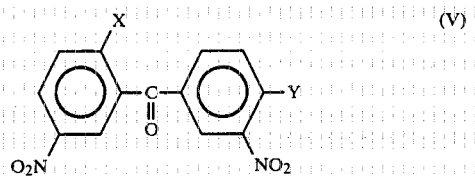
(V)

in which X and Y are the same or different halogen atoms.

6. The process according to claim 1 in which the benzophenone compounds of the general formula (I) are a mixture of dinitro-dichloro benzophenones obtained from a nitration of a product of a Fiedle-Crafts' reaction of 2-chloro benzoylchloride and/or 4-chloro benzoylchloride with chlorobenzene.

7. The process according to claim 2 in which the benzophenone compound of the general formula (II) is 3,3'-dinitro-4,4'-dichloro benzophenone obtained from a nitration of 4,4'-dichloro benzophenone in a fatty halogenated hydrocarbon solvent.

* * * * *

UNITED STATES PATENT AND TRADEMARK OFFICE
CERTIFICATE OF CORRECTION

PATENT NO. : 4,556,738
DATED : December 3, 1985
INVENTOR(S) : Saburo Kawashima et al It is certified that error appears in the above-identified patent and that said Letters Patent is hereby corrected as shown below:

Col. 1, line 55; "recrystallation" should read
-- recrystallization -- .

Col. 3, line 67; " + " should read -- " ' " -- .

Col. 6, line 48; "range of 40°-80°C." should read
-- range of 20° to 100°C. -- .

Col. 14, line 39; "is filtered" should read -- are filtered -- .

Col. 18, line 54; "is subject" should read -- is subjected -- .

Col. 19, line 23; "yield" should read -- yields -- .

Col. 20, line 38; "is filtered" should read -- are filtered -- .

UNITED STATES PATENT AND TRADEMARK OFFICE
CERTIFICATE OF CORRECTION

PATENT NO. : 4,556,738
DATED : December 3, 1985
INVENTOR(S) : Saburo Kawashima et al It is certified that error appears in the above-identified patent and that said Letters Patent is hereby corrected as shown below:

Col. 21, line 52; "order to the catalyst" should read

-- order to remove the catalyst -- .

Col. 22, Claim 1, the formula:

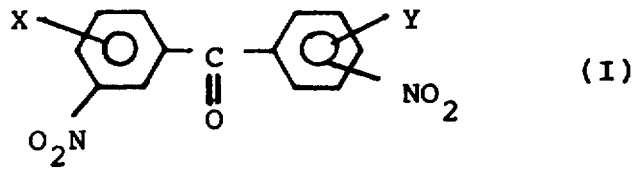

should read --

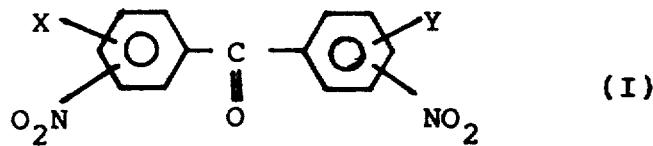

-- .

UNITED STATES PATENT AND TRADEMARK OFFICE
CERTIFICATE OF CORRECTION

PATENT NO. : 4,556,738
DATED : December 3, 1985
INVENTOR(S) : Saburo Kawashima et al It is certified that error appears in the above-identified patent and that said Letters Patent is hereby corrected as shown below:

Col. 22, Claim 4, the formula:

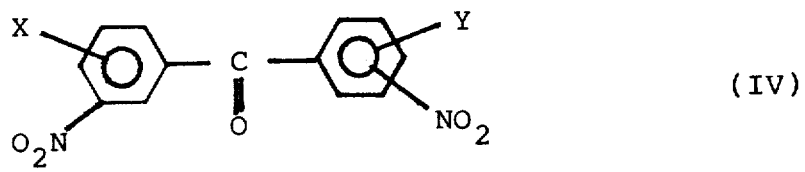

(IV)

should read --

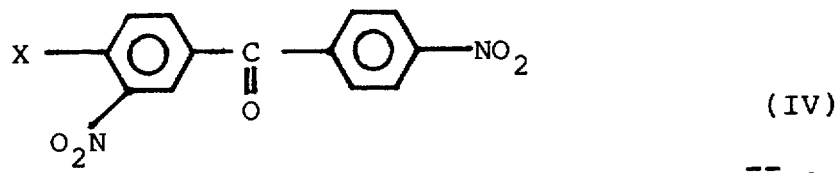

(IV)

-- .

Col. 24, Claim 6, line 4; "Fiedle" should read -- Friedle -- .

Signed and Sealed this

Eighth Day of July 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,556,738

DATED : Dec. 3, 1985

INVENTOR(S) : Saburo KAWASHIMA, Akihiro YAMAGUCHI, Keizaburo YAMAGUCHI, Kenichi SUGIMOTO, Yoshimitu TANABE It is certified that error appears in the above-identified patent and that said Letters Patent is hereby corrected as shown below:

Cover page, Item [75], should read:

—Saburo Kawashima, Yokosuka, Japan; Akihiro Yamaguchi, Kamakura, Keizaburo Yamaguchi, Kawasaki, Kenichi Sugimoto, Yokohama, Yoshimitu Tanabe, Yokohama, all of Japan.—

Signed and Sealed this

Eighteenth Day of October, 1994

Attest:

BRUCE LEHMAN

*Attesting Officer*  *Commissioner of Patents and Trademarks*